US009199238B2

(12) United States Patent
Koltzscher et al.

(10) Patent No.: US 9,199,238 B2
(45) **Date of Patent: *Dec. 1, 2015**

(54) DEVICE FOR ANALYSING A CHEMICAL OR BIOLOGICAL SAMPLE

(71) Applicants: CARPEGEN GMBH, Muenster (DE); SYSTEC ELEKTRONIK UND SOFTWARE GMBH, Muenster (DE)

(72) Inventors: Max Koltzscher, Muenster (DE); Antje Roetger, Muenster (DE); Krzysztof Wlodzimierz Siemieniewicz, Maastricht (NL); Jens Heitmann, Greven (DE); Christoffer Mai, Gelsenkirchen (DE); Klaus-Gerd Schoeler, Nottuln (DE); Tilmann Wolter, Muenster (DE)

(73) Assignees: CARPEGEN GMBH, Muenster (DE); SYSTEC ELEKTRONIK UND SOFTWARE GMBH, Muenster (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/663,471

(22) Filed: Mar. 20, 2015

(65) Prior Publication Data

US 2015/0190812 A1 Jul. 9, 2015

Related U.S. Application Data

(63) Continuation of application No. 13/003,016, filed as application No. PCT/EP2009/005031 on Jul. 10, 2009, now Pat. No. 9,011,796.

(30) Foreign Application Priority Data

Jul. 10, 2008 (EP) .................................... 08012523

(51) Int. Cl.
*C12Q 1/68* (2006.01)
*B01L 7/00* (2006.01)
*B01L 3/00* (2006.01)

(52) U.S. Cl.
CPC ........... *B01L 7/5255* (2013.01); *B01L 3/50273* (2013.01); *B01L 3/502715* (2013.01); *B01L 3/502738* (2013.01); *B01L 2200/10* (2013.01); *B01L 2300/0636* (2013.01); *B01L 2300/0803* (2013.01); *B01L 2300/0809* (2013.01); *B01L 2300/0861* (2013.01); *B01L 2300/0877* (2013.01); *B01L 2300/18* (2013.01); *B01L 2400/0481* (2013.01); *B01L 2400/0487* (2013.01); *B01L 2400/065* (2013.01); *B01L 2400/0622* (2013.01); *B01L 2400/0644* (2013.01)

(58) Field of Classification Search
CPC .......... B01L 7/5255; B01L 2300/0803; B01L 2300/0809; B01L 2400/065; B01L 2400/0481; B01L 2400/0487; B01L 2400/0622; B01L 2400/0644; B01L 2300/0861; B01L 3/502738
USPC .................. 422/501–505, 509, 516; 436/180
See application file for complete search history.

*Primary Examiner* — Shogo Sasaki
(74) *Attorney, Agent, or Firm* — Norman B. Thot

(57) ABSTRACT

A microfluidic device of a microfluidic apparatus for analyzing a fluidic sample includes at least two support members comprising a first support member and a second support member. The first support member comprises a first support member chamber configured to hold a fluid. The second support member comprises a second support member chamber configured to hold a fluid. The first support member and/or the second support member perform a movement with respect to each other to connect a first support member conduit with a second support member conduit, and to connect the first support member chamber with the second support member chamber. A pump element effects a transfer of the fluid from the first support member chamber to the second support member chamber and/or vice versa. A connection of the first support member chamber, the second support member chamber, and the pump element creates a closed fluidic circuit.

16 Claims, 10 Drawing Sheets

DEVICE FOR ANALYSING A CHEMICAL OR BIOLOGICAL SAMPLE

CROSS REFERENCE TO PRIOR APPLICATIONS

This application is a continuation of application Ser. No. 13/003,016, filed on May 3, 2011, which is a U.S. National Phase application under 35 U.S.C. §371 of International Application No. PCT/EP2009/005031, filed on Jul. 10, 2009 and which claims benefit to European Patent Application No. 08012523.0, filed on Jul. 10, 2008. The International Application was published in English on Jan. 14, 2010 as WO 2010/003690 A1 under PCT Article 21(2).

FIELD

The present invention relates to a device and a method for analysing a chemical or biological sample, in particular a sample of biological origin, e.g., a biological sample comprising nucleic acids. The present invention furthermore relates to the field of "lab-on-the-chip" technology suitable for "in-field" and "point-of-care" (POC) applications.

BACKGROUND

Highly sophisticated chemical, biochemical or molecular biology based analyses, such as nucleic acid testing, NAT, in particular all modifications of polymerase chain reaction (PCR), become more and more attractive in medicine and health care as well as in nearly all fields of industry, including agriculture, biotechnology, chemical and environmental businesses. There is a great demand for analytical methods capable of satisfying the increasing requirements concerning, for instance, therapeutic outcome or planning and controlling of industrial manufacturing processes and costs.

Most of the state-of-the-art analytical systems are very complex, require handling of unstable reagents, expensive laboratory equipment and as well as highly trained personnel to conduct and interpret the testing. The analysis is therefore usually neither time-nor cost-effective as it involves sending a specimen to a specialised laboratory with considerable delay in obtaining results. For this reason, in-field and point-of-care testing (POCT) have become particularly desirable as they significantly shorten sampling-to-result time. In clinical diagnostic, some asymptomatic patients are likely to become impatient with the testing process and fail to attend the follow up appointment, thus should be offered proper treatment or reassurance during a single visit. There is also a prompt need for rapid, easy-to-perform tests for other in-field applications, e.g., forensic testing ("scene-of-crime", "point-of-arrest"), food testing (GMO detection, food fraud), defence (biothread detection) and many more.

Lab-processed nucleic acid testing (NAT) has to date generally had much greater sensitivity than rapid POC tests, being usually based on pathogen immunodetection. Most of the NAT-based platforms and technologies currently under development do not provide an integrated solution for sample preparation, analysis and data evaluation. An example of a successful platform is described in WO 2005/106040 A2. Said device, however, requires manual loading of reagents which can be inconvenient for the user and error-prone. The data evaluation also requires operator intervention. It is therefore inappropriate for in-field testing. Further the complex lab-in-a-box design of the device, which consists of several large injection moulded parts and further several mounting parts such as filters, screws, and nuts, etc., results in high costs for the disposable device.

SUMMARY

An aspect of the present invention is to provide a device for analysing a chemical or biological sample which avoids at least one of the disadvantages of the devices known from the state of the art. An aspect of the present invention is to provide a device which enables for a rapid testing, is easy to handle, and which is not that expensive to produce.

In an embodiment, the present invention provides a microfluidic device of a microfluidic apparatus for analyzing a fluidic sample which includes at least two support members comprising a first support member and a second support member. The first support member comprises at least one first support member chamber configured to hold a fluid. The at least one first support member chamber comprises at least two first support member chamber openings comprising a first first support member chamber opening and a second first support member chamber opening, and at least two first support member conduits comprising a first first support member conduit, and a second first support member conduit. The first first support member conduit is connected to the first first support member chamber opening, and the second first support member chamber conduit is connected to the second first support member chamber opening. The second support member comprises at least one second support member chamber configured to hold a fluid. The at least one second support member chamber comprises at least two second support member chamber openings comprising a first second support member chamber opening and a second second support member chamber opening, and at least two second support member conduits comprising a first second support member conduit, and a second second support member conduit. The first second support member conduit is connected to the first second support member chamber opening, and the second second support member chamber conduit is connected to the second second support member chamber opening. The first support member and/or the second support member are configured to perform a movement with respect to each other so as to connect one of the at least two first support member conduits with one of the at least two second support member conduits and to thereby connect the at least one first support member chamber with the at least one second support member chamber. A pump element is arranged in at least one of the at least two support members. The pump element is configured to connect to the at least one first support member chamber via one of the at least two first support member conduits and/or to the at least one second support member chamber via one of the at least two second support member chamber conduits, and to effect a transfer of the fluid from the at least one first support member chamber to the at least one second support member chamber and/or a transfer of the fluid from the at least one second support member chamber to the at least one first support member chamber. A connection comprising the at least one first support member chamber, the at least one second support member chamber, and the pump element via the at least two first support member conduits and the at least two second support member conduits creates a closed fluidic circuit.

BRIEF DESCRIPTION OF THE DRAWINGS

The present invention is described in greater detail below on the basis of embodiments and of the drawings in which.

DETAILED DESCRIPTION

Figure 1:
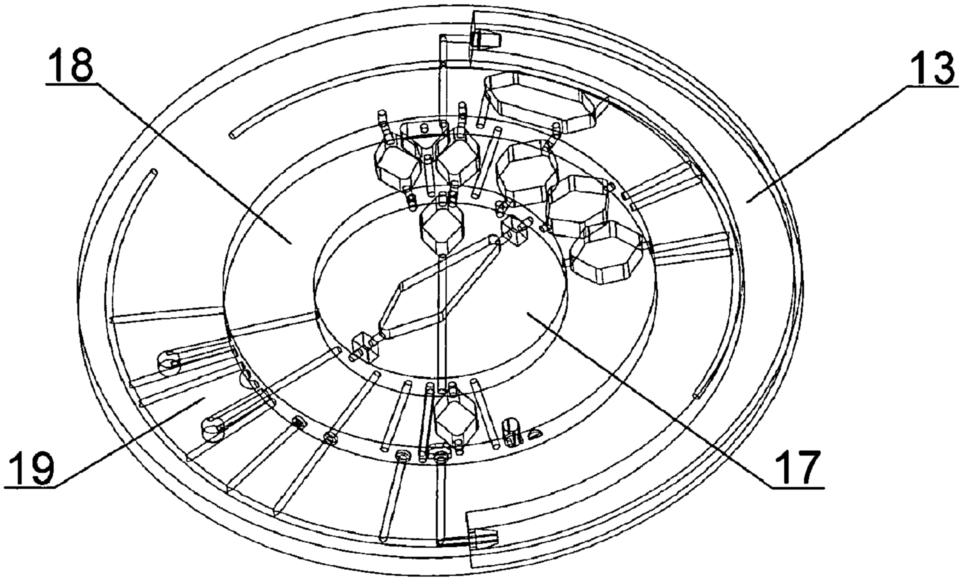
FIG. 1: shows an isometric view of a device according to the present invention in a first embodiment.

The present invention provides a device for analysing a sample, said device comprising at least one depot chamber for receiving one or more reagents and at least one process chamber, whereas the depot chamber is connectable with the process chamber. The device is further characterized in that the process chamber is integrated in a first support member and the depot chamber is integrated in at least a second support member, whereas the support members are arranged in that the process chamber is connectable with the depot chamber by a relative movement of the first and second support members with respect to each other. According to the present invention, a pump element is further provided, which (temporarily) creates a pressure sufficient for transferring a substance which is located inside the device from one chamber to another. The pump element is integrated into one of the support members, i.e., it is part of the device itself.

One or more depot and/or process chambers are possible. The chambers can, for example, be reversibly connectable.

The device for analysing a sample according to the present invention provides a simple and non-complex design, and in particular a design which can be inexpensively produced. The present invention thus also provides a device which suitably allows the use as a "disposable", i.e., a lab on a chip which is disposed after use. Accordingly the device of the present invention is particularly suitable for in-field and point-of-care settings. Further, by integrating the pump element into the device itself, all elements which will contact the substances during analysis are combined in a—for example, disposable—unit, which allows for the creation of a closed fluidic system, which helps preventing any contamination of the substances or the interior of the device itself. Such contamination may occur when the device would have to be connected to an "exterior" pump.

The chamber of the device can be pre-filled with reagents adapted to perform a distinct analysis. The device can thereby be used as a "ready-to-use" format of a lab on a chip.

The sample analysed in the device of the present invention can be of any origin or nature, for example, of biological, natural, synthetic or semi-synthetic origin. The present invention is thus not limited to any specific sample origin.

In an embodiment of the present invention, an elastic hose can, for example, be provided as part of the pump element. The elastic hose may be connected to the chambers by respective conduits which are integrated into the support members. A pumping pressure may be created inside the elastic hose by locally deforming and thereby reversibly sealing it, for example, by means of a roller element, which is moved along the length of the elastic hose. This creates a positive pressure inside the elastic hose on the side of the roller element which faces in the direction of movement. A negative pressure is thereby created on the opposite side inside the elastic hose.

The term "elastic hose" according to the present invention may cover all elements which define an interior space and have an elastic shell surrounding said interior space and further at least one inlet and one outlet. In an embodiment, the elastic hose according to the present invention can, for example, have an elongate, pipe-like shape, although other shapes are also possible.

In an embodiment of the present invention, the chambers can, for example, be connected to the pump element in order to create a closed loop circuit if the support members are in a relative position in which the chambers are connected to each other. The closed fluidic loop on the one hand avoids any contamination of the substances inside the chambers and further allows in a simple manner for a reversion of the direction of flow of said substances.

According to the present invention, the relative movement of the support members connecting the chambers with each other can be of various nature, e.g., the chambers can be interconnected via a linear, diagonal, arcuate, circular or the like movements of the support members, or combinations thereof. The chambers of the device can hence be located in one or more levels or sections and the device can comprise a sequence of support members, including chambers which extend through different levels or different sections of one level.

The depot or process chambers according to the present invention are not limited in number, size, shape (e.g., cubic, rhombic, meander-like, etc.), material or any other physical property like e.g., coatings or isolations. Their individual design is suitably adapted to the nature of the sample to be processed or the process step, which the chamber is used for. For example, in case the device of the present invention is used for nucleic acid testing (NAT), the process chamber may comprise a nucleic acid binding matrix; at least one isolation reagent and one analysing reagent are furthermore located in different depot chambers. When amplifying nucleic acids using polymerase chain reaction (PCR), a large surface/volume ratio of the respective reaction chamber can, for example, be provided to improve thermal cycling efficiency.

In an embodiment of the present invention, the first support member can, for example, be formed as a circular element and the second support member is formed as an annular element, whereas the circular and annular elements are concentrically located with respect to each other. This embodiment excels by its compact, disc-like shape. Because the first and second support members can be rotated with respect to each other, a relative movement of the members can furthermore be achieved without any variation to its outside dimensions. This is of special advantage in terms of the device being integrated into a complex apparatus for automation (e.g., a base station).

In an embodiment of the present invention, a third support member can, for example, be provided that is movable with respect to the second support member. The third support member can, for example, be formed as an annular disc, which is concentrically arranged and rotatable with respect to the first and/or second support member.

In one embodiment of the present invention, support members form a seal upon assembly, thus providing a substantially closed fluidic system within the device. Simultaneously, in order to allow the successive process steps to be carried out, the support members within such an assembled device can be rotatable (or movable) with respect to each other. Further, it is advantageous that the sealing is achieved by providing an optimal direct contact between the support members within the assembled device, with no additional gasket material necessarily required. The support members can, for example, thus be made of suitable polymer materials, such as polyoxymethylene (POM), polyethylene (PE), polycarbonate (PC), polytetrafluoroethylene (PTFE) or cyclic olefin copolymer (COC).

In order to allow a visual, optical or any other form of an image-related evaluation of the test or analysis results, the device of the present invention may be at least partially constituted of a transparent material, for example, a transparent polymer, therewith allowing the observation of the reaction chamber or other parts of the device (including conduits).

The device according to the present invention may advantageously be used with a base station, whereas that base station can comprise at least one drive for moving the support members with respect to each other. The base station may further comprise a pump drive. Such a system comprising at least a base station and a separate analysing device provides the advantage that complex and thus expensive technical devices can be incorporated into the base station, whereas the analysing device may be designed as a cheap disposable. This decreases the costs involved with the use of the analysing device or, respectively, the system according to the present invention.

In an embodiment of the present invention, the pump element of the device can, for example, comprise an elastic hose, and the pump drive of the base station can, for example, comprise a deformation element, for example, a roller element, which is moved along the length of the elastic hose, thereby locally deforming the elastic hose. This embodiment is advantageous in that the complex and expensive parts of the pump (which comprises the pump element of the device and the pump drive of the base station) are situated in the base station and only the elastic hose is part of the (for example) disposable device. The cost of production for the device can therefore be kept low.

In case the base station further comprises a control and evaluation unit, the control of the drive(s) of the base station may be automated. This allows for a full automation of the analysing processes executed within the device.

The system according to the present invention may further comprise at least one heating means. Said heating means may generate different temperature zones in the base station. The base station may further comprise a drive by which said temperature zones are movable with respect to the device. The temperatures inside the different chambers of the device may therefore be adjusted to values which are best suited for the respective process steps carried out inside said chambers. This allows generating a temperature profile which is adapted to the successive process steps being conducted within the analysing device.

A method for analysing a sample according to the present invention comprises the step of inserting the sample into an analysing device according to the present invention and a sequence of processes (analysing the sample within said device, data acquisition, data processing and finally results reporting) being executed with the aid of a base station according to the present invention. In one embodiment, the first step can be a manual step, whereas the other steps can be fully or partly automated.

The present invention can, for example, exhibit several advantages compared to devices known from the prior art. The device (respectively system) according to the present invention permits an easy and safe use even by untrained staff. For example, all process steps, including sample preparation and analysis as well as data evaluation and results calling, can be integrated and can be executed automatically. The use of a disposable device, which is prefilled with all reagents required for the entire process, eliminates the risk of human error or cross contamination, while the compact design of the device reduces the quantity of waste material. In particular, if the device is constructed as substantially closed system, the risk of contamination of reagents as well as the risk of amplicon contamination of the environment is substantially reduced.

The present invention will be explained in further detail with reference to specific embodiments as shown in the drawings.

FIG. 1 shows a first embodiment of a device for analysing a sample according to the present invention. The device includes a liquid system for the isolation and analysis of nucleic acids from a chemical or biological sample. The device further comprises three support members; the first support member 17 is shaped as a thin circular disc, i.e., the diameter of the circular disc exceeds by far its thickness. The second support member 18 is shaped as an annular disc that is concentrical with respect to the first support member. The first and second support members 17, 18 may be rotated with respect to each other about their common central axis. The third support member 19 is shaped as an annular disc as well; it encloses the second support member 18 and is concentrical with respect to the first and second support member 17, 18. The outer diameter of the third support member 19 is about 10 cm.

Possible materials for the support members are polymers, such as polyoxomethylene (POM), polyethylene (PE), polycarbonate (PC), polytetrafluoroethylene (PTFE) or cyclic olefin copolymer (COC). To seal the fluidic connections between the single parts of the device, a thin layer of elastic polymer is provided on both interfaces of the second support member 18. In order to create the thin layer, the second support member 18 can, for example, be produced by two-component injection moulding, whereas the other support members are fabricated by any method known in the art, such as injection moulding, hot embossing or microfabrication. The parts are produced with an oversize in diameter. To create a fitting connection of all three parts, the assembly can be done with the help of thermal expansion and contraction. The inner part is cooled down to reduce the diameter whereas the outer part is heated up to increase the diameter. After assembly and temperature balance, both parts are accurately fitting and the seal is compressed to ensure leak tightness.

Incorporated into the three support members 17, 18, 19 are a number of chambers being sized and shaped differently, and further functional components. The three support members comprise:

- a first depot chamber 1, housing a lysis buffer containing sodium dodecyl sulfate (SDS) and proteinase K in a total amount of approximately 100 µl;
- a second depot chamber 2, housing a binding buffer comprising at least 3 M NaCl and at least 1% Tween 20 in a total amount of approximately 300 µl;
- a third depot chamber 3, housing a first purifying agent comprising at least 3 M NaCl in a total amount of approximately 200 µl;
- a fourth depot chamber 4A, housing a first amount of a second purifying agent comprising at least 50% of ethanol in a total amount of approximately 200 µl;
- a fifth depot chamber 4B, housing a second amount of a second purifying agent comprising at least 50% of ethanol in a total amount of approximately 200 µl;
- a sixth depot chamber 5, housing an elution buffer comprising either a TE buffer or distilled water in a total amount of approximately 200 µl;
- a sample chamber 6, having a capacity of about 100 µl;
- a process chamber 7, housing the DNA binding matrix of magnetic silica particles and having a capacity of about 400 µl;
- a waste chamber 8, which has a capacity of about 400 µl;
- ten mastermix depot chambers 9 (only one is shown in FIGS. 1 to 14), housing substances for the amplification and detection of nucleic acids in a total amount of 16 to 18 µl (in the presented embodiment, liquid reagents are used for the PCR although other formulations (encapsulated, freeze-dried, air-dried, etc.) are equally suitable and may be preferred due to their prolonged stability, even at elevated temperatures (e.g., during storage or transportation of the point-of-care device)—in this case the capacities of the sixth depot chamber 5 and the measuring loops 14 may need to be adjusted in order to ensure a proper rehydration of the reagents);
- ten PCR reaction chambers 10 (only two are shown in FIGS. 1 to 14) which are used for the amplification and detection of nucleic acids, each having a capacity of 20 µl;
- an elution chamber 11, which is not prefilled and has a capacity of about 100 µl;
- two ports 12 for an elastic hose (not shown) acting as a pump element;
- ten measuring loops 14 of conduits (only two are shown in FIGS. 1 to 14), each having a capacity of about 4 µl;
- filling ducts 15 (only three pairs are shown in FIG. 1 to FIG. 14); and
- a ventilation channel 16.

In an alternative embodiment the depot chambers 1 to 3 may be filled with the following substances:

- first depot chamber 1: a lysis buffer with >1 M GuHCl (or GuSCN), >1% Tween 20 (or Triton X-100), SDS, Proteinase K, in a total amount of 100 µl;
- second depot chamber 2: a binding buffer with >3 M GuHCl (or GuSCN), in an total amount of 50 µl; and
- third depot chamber 3: a first purifying agent with >3 M GuHCl (or GuSCN) and >30% ethanol, in an total amount of 200 µl.

The third support member 19 further comprises a curved opening 13 for receiving an elastic hose (not shown) as part of the pump element. The elastic hose is made of silicone and it is connected to the two ports 12, which are connected to a net of conduits, said conduits being incorporated into the three support members. The conduits connect the different chambers of the support members in a way which will become apparent by the following, more detailed description of the use of the device. The pump element operates as a roller pump; the elastic hose is compressed by means of a roller element 23, which is part of a base station (cf. FIG. 15A and FIG. 15B), in which the device is placed for processing, said roller element being moved by means of a pump drive of the base station along the length of the elastic hose. Due to the movement of the roller element, a positive pressure is generated inside the elastic hose on one side of the roller element and consequently a negative pressure is generated inside the elastic hose on the opposite side of the roller element. The elastic hose of the pump element creates a closed loop with the conduits and the different chambers which are connected to the elastic hose in the respective position of the first and second support member 17, 18. The closed loop reduces the risk of a contamination.

Figure 2:
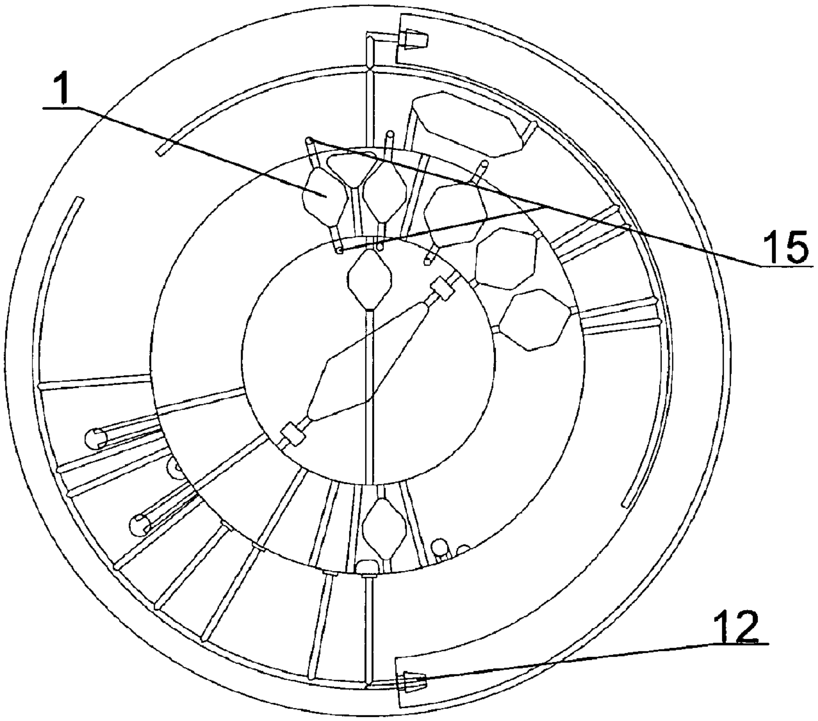
FIG. 2 shows a processing step while using the device according to FIG. 1.

The device as shown in FIG. 1 is an inexpensive disposable, which is prefilled with all the substances for the sample preparation, as well as with all the substances needed for a real-time quantitative PCR analysis. The liquid substances may be filled into the device through filling ducts 15 incorporated into the support members. FIG. 2 shows the three support members of the device in a respective reagent loading position (for a better overview, only three pairs of filling ducts are shown). In an alternative embodiment, the support members may be designed with the chambers being open to one side. The open chambers may then be easily filled with dry reagents (e.g., encapsulated, freeze-dried, air-dried, etc.) and afterwards sealed by an adhesive foil, which is attached to the open side of the support members to form closed chambers.

For the transportation and handling of the device, the three support members may be rotated such that the conduits leading to and from the different prefilled chambers are separated from any connecting conduit in the adjacent support member, thus sealed.

The applied method for the isolation of the DNA is based on the principle of binding nucleic acids to the silica surface in the presence of highly concentrated salt solutions. The magnetic silica particles, which are housed inside the process chamber 7, act as a matrix for binding the DNA.

FIGS. 2 to 14 show different steps during the use of the device of FIG. 1.

Figure 3:
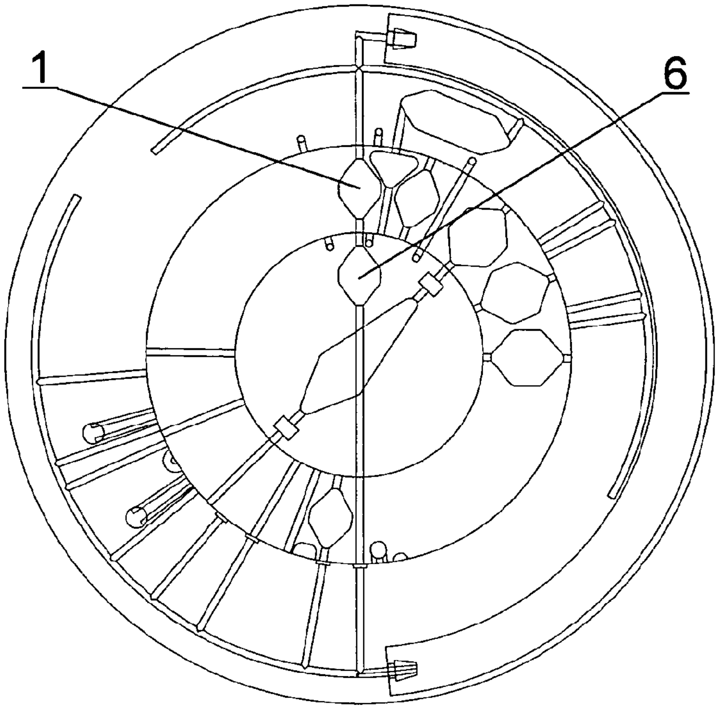
FIG. 3 shows a processing step while using the device according to FIG. 1.

First a sample containing the bacteria is collected, for example, from the oral cavity of a patient, and is placed inside the sample holding chamber 6. Afterwards, the sample holding chamber 6 is sealed by means of an adhesive film. The whole device is then placed inside the base station (FIGS. 15A and 15B), and the automatic analysing process is initiated. FIG. 3 shows the three support members of the device in a starting position.

By means of the drive of the base station, the second support member 18 is rotated with respect to the first and third support member 17, 19 in a clockwise direction, as is shown in FIG. 3. Due to the movement of the second support member 18, a first loop is created which connects the elastic hose of the pump element with the first depot chamber 1 and the sample chamber 6. The lysis buffer, which was contained in the first depot chamber 1, is accordingly moved repeatedly from the first depot chamber 1 into the sample chamber 6, and vice versa, as the roller element of the pump element is moved repeatedly along the length of the elastic hose. The back and forth moving of the lysis buffer aims at mixing it with the sample. The mixture is meanwhile heated in the sample chamber 6 to a temperature of 55° C. to 95° C. for a period of approximately 5 to 15 minutes. The mixture is then moved back to the first depot chamber 1.

Figure 4:
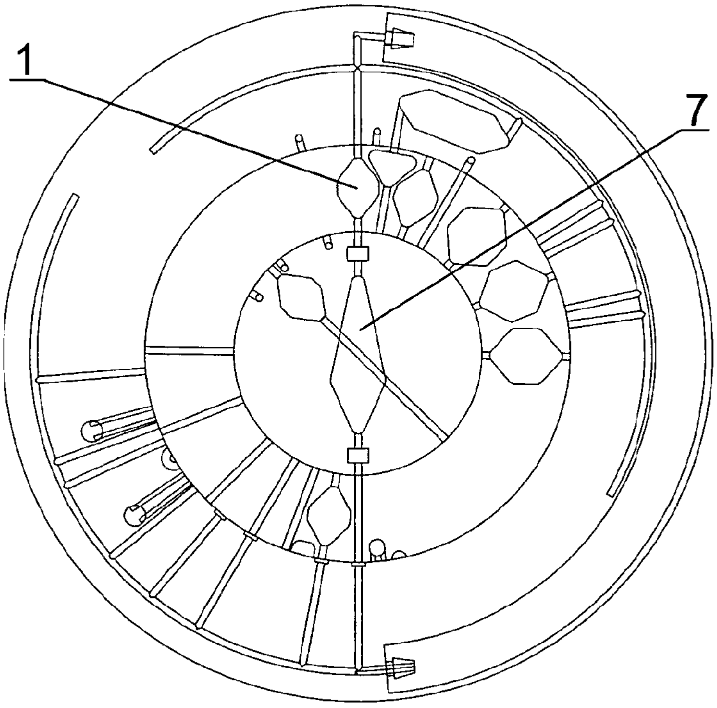
FIG. 4 shows a processing step while using the device according to FIG. 1.

FIG. 4 shows the device after a counter clockwise rotation of the first support member 17 which results in a connection of the first depot chamber 1 with the process chamber 7. The process chamber 7 contains the DNA binding magnetic silica particles (not shown). Further embodiments may provide a membrane or a fleece filter as DNA binding matrix. The lysate is pumped form the first depot chamber 1 into the process chamber 7.

Inside the process chamber 7, a magnetic agitator 33 is located (cf. FIG. 16), which supports the mixing of the substances inside the process chamber 7. The magnetic agitator 33 is rotated at high rotational speed by means of a spinning external permanent magnet 20, which is part of the base station (cf. FIG. 15A) and rotationally driven by an electric motor 21.

Figure 5:
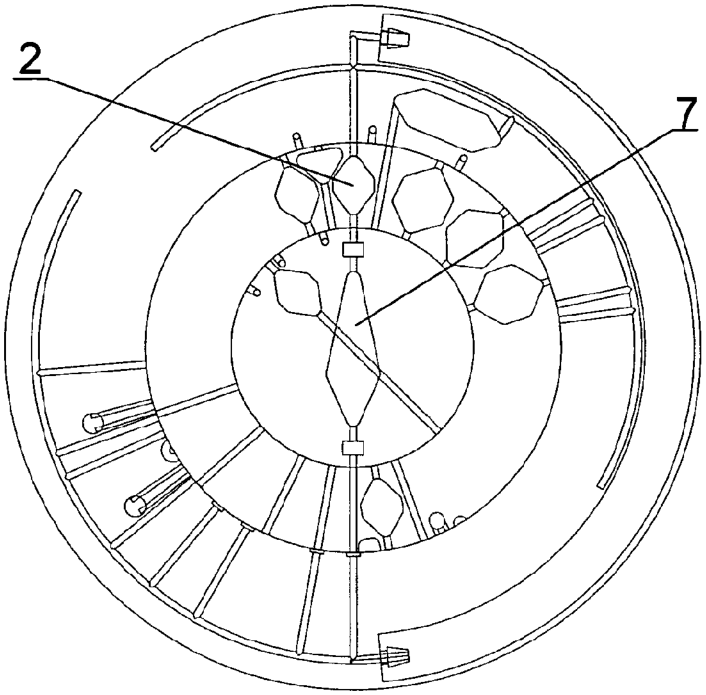
FIG. 5 shows a processing step while using the device according to FIG. 1.

FIG. 5 shows the device after a further sectional rotation of the second support member 18 in a counter clockwise direction. In this position the process chamber 7 is connected to the second depot chamber 2 which contains the binding buffer. The binding buffer is pumped from the second depot chamber 2 into the process chamber 7. During a period of up to 5 minutes the binding buffer and the lysate are stirred in the process chamber 7 by means of the magnetic agitator 33 and the spinning external permanent magnet 20 for achieving a good mixing of the components and a good binding of the DNA to the magnetic silica particles. This process step is carried out at room temperature.

Figure 6:
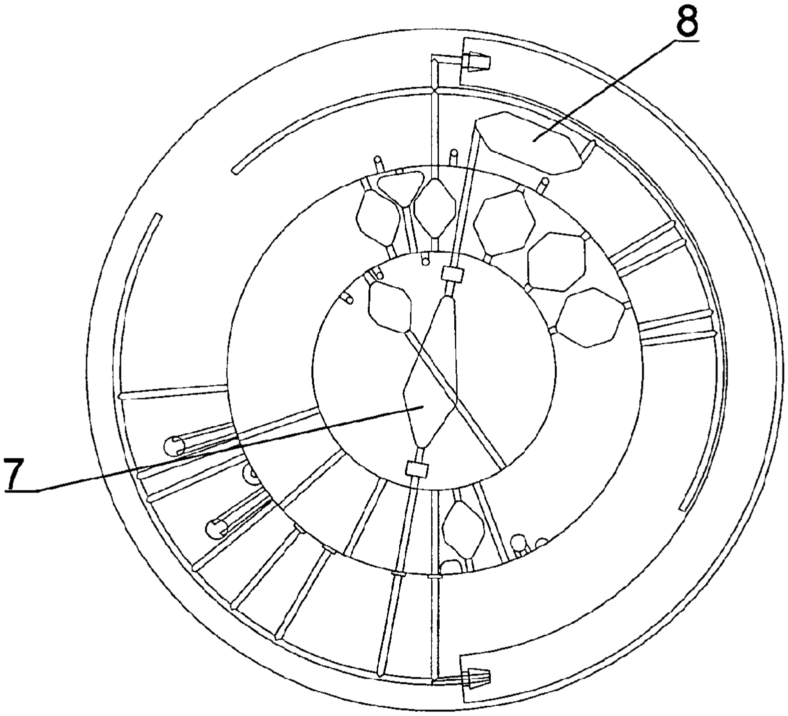
FIG. 6 shows a processing step while using the device according to FIG. 1.

The next position as shown in FIG. 6 is reached by a further rotational movement of the first support member 17 in a clockwise direction, by which the process chamber 7 is connected to the waste chamber 8. The binding buffer and the lysate (which no longer contains the DNA) are moved to the waste chamber 8, while the magnetic silica particles and the DNA are retained in the process chamber 7 by means of the non-spinning external magnet 20.

Figure 7:
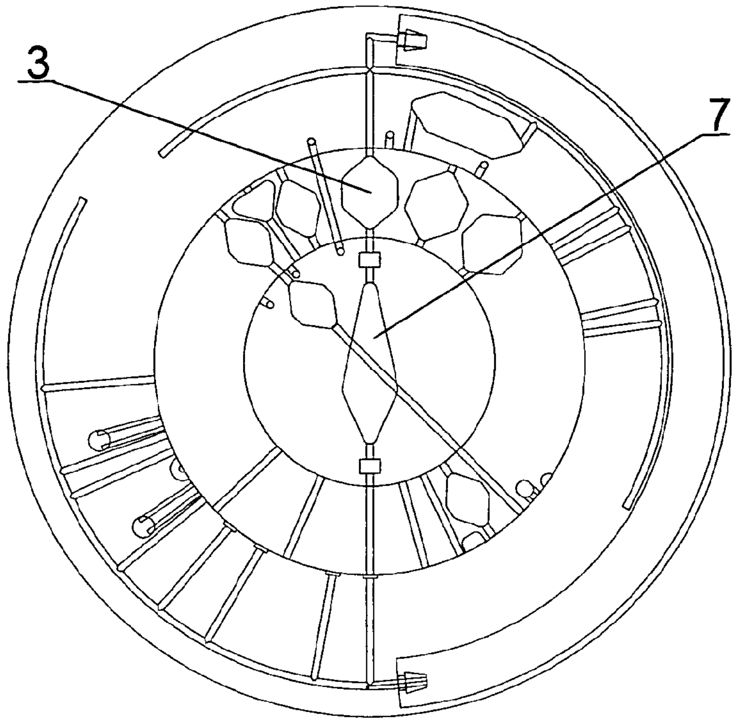
FIG. 7 shows a processing step while using the device according to FIG. 1.
Figure 8:
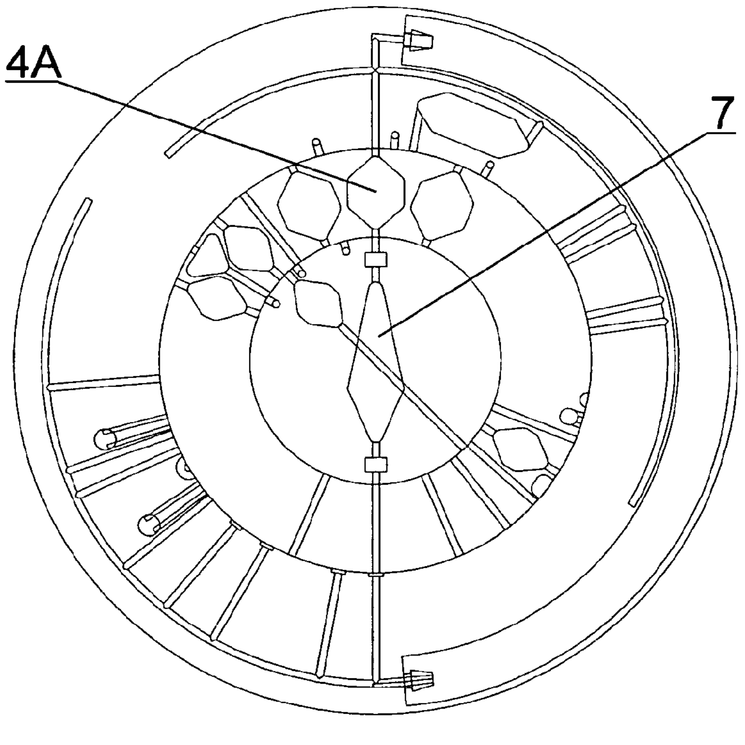
FIG. 8 shows a processing step while using the device according to FIG. 1.
Figure 9:
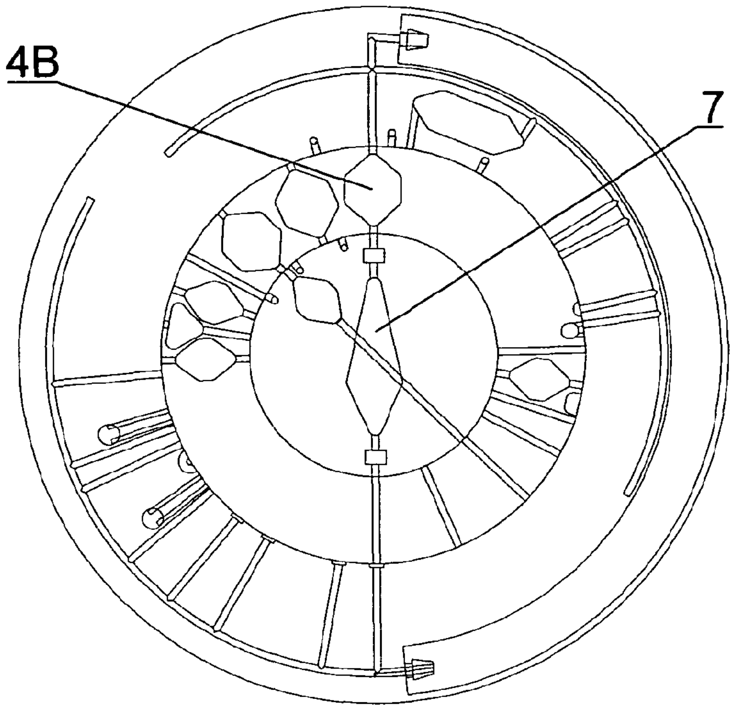
FIG. 9 shows a processing step while using the device according to FIG. 1.

After a further rotational movement of the first and the second support member 17, 18 in a counter clockwise direction, the process chamber 7 is connected to the third depot chamber 3 which contains the first purifying agent comprising NaCl (cf. FIG. 7). The first purifying agent is pumped from the third depot chamber 3 into the process chamber 7, which comprises DNA bound to the magnetic silica particles. The particles are then resuspended in the purifying agent by means of the magnetic agitator 33 and the spinning external permanent magnet 20. In doing so, leftovers of the buffers from the sample preparation, and further cell detritus, proteins, etc. are removed from the DNA bound to magnetic silica particles. The purifying agent along with the impurities is then moved back into the third depot chamber 3, whereas the DNA bound to magnetic silica particles is retained in the process chamber 7 by means of the non-spinning external magnet 20.

After a further rotational movement of the second support member 18 (cf. FIG. 8), the process chamber 7 is connected to the fourth depot chamber 4A containing a first amount of the second purifying agent, which comprises at least 50% of ethanol. For a further purification of the DNA bound to magnetic silica particles, the second purifying agent is moved from the fourth depot chamber 4A to the process chamber 7. The particles are then resuspended in the purifying agent by means of the magnetic agitator 33, and the spinning external permanent magnet 20. Unwanted leftovers from the sample preparation and the first purification step are thereby removed. After a sufficient purification of the DNA bound to magnetic silica particles, the purifying agent along with the impurities is moved back to the fourth depot chamber 4A, whereas the magnetic silica particles with bound DNA are retained in the process chamber 7 by means of the non-spinning external magnet 20.

After a further rotational movement of the second support member 18 in a counter clockwise direction (cf. FIG. 9), the process chamber 7 is connected to the fifth depot chamber 4B, which contains a second amount of the second purifying agent (comprising at least 50% of ethanol). For a further purification of the silica particles, the second purifying agent is moved from the depot chamber 4B to the process chamber 7. The particles are then again resuspended in the purifying agent by means of the magnetic agitator 33 and the spinning external permanent magnet 20. After a sufficient purification of the DNA bound to magnetic silica particles, the purifying agent along with the impurities is moved back to the fifth depot chamber 4B, whereas the silica particles and the DNA remain in the process chamber 7, being retained by means of the non-spinning external magnet 20.

Figure 10:
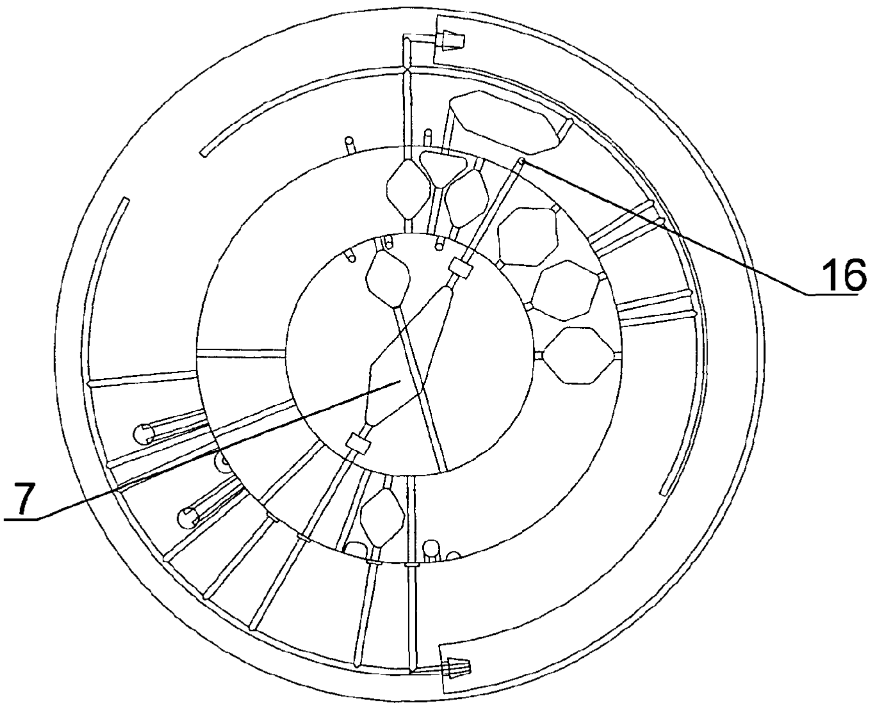
FIG. 10 shows a processing step while using the device according to FIG. 1.

Then the first and second support members 17, 18 are rotationally moved in a clockwise direction to connect the process chamber 7 via the ventilation channel 16 with the atmosphere (cf. FIG. 10). Incorporated into the ventilation channel is a filter (not shown) which prevents any leak of aerosols. The process chamber 7 is heated to a temperature of approximately 55° C. and vented for a period of about 5 minutes with air. Leftovers of alcohol from the second purifying agent are thereby removed.

Figure 11:
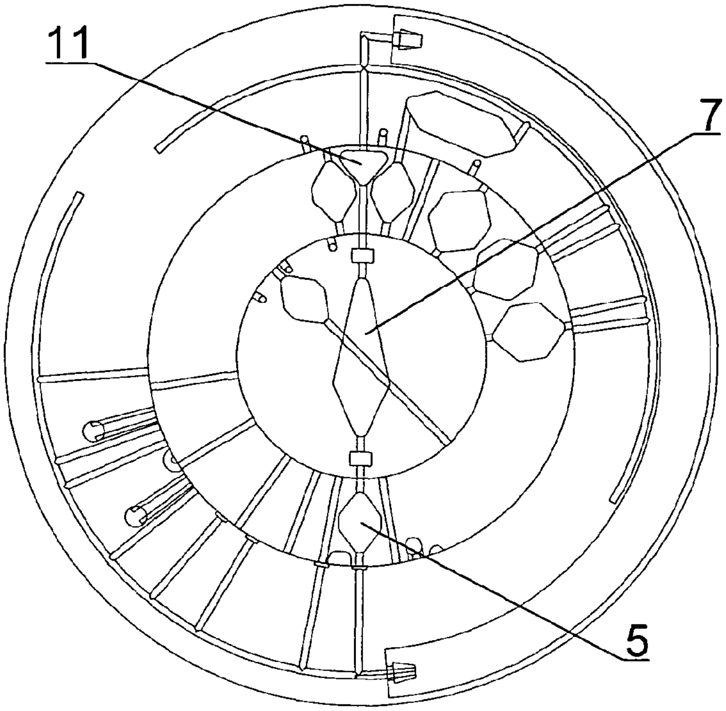
FIG. 11 shows a processing step while using the device according to FIG. 1.

Through a further rotational movement of the first and second support member 17, 18 in a counter clockwise direction, the sixth depot chamber 5 and the support chamber 11 are connected to the process chamber 7 (cf. FIG. 11). The elution buffer from the sixth depot chamber 5 is pumped into the elution chamber 11 via the process chamber 7, thereby releasing the DNA from the magnetic silica particles. This process takes place at a temperature of approximately 55° C. and for a period of about 5 minutes. Afterwards, the elution buffer and the DNA are moved back from the elution chamber 11 to the sixth depot chamber 5, and the magnetic particles are retained in the process chamber 7 by means of the non-spinning external magnet 20.

Figure 12:
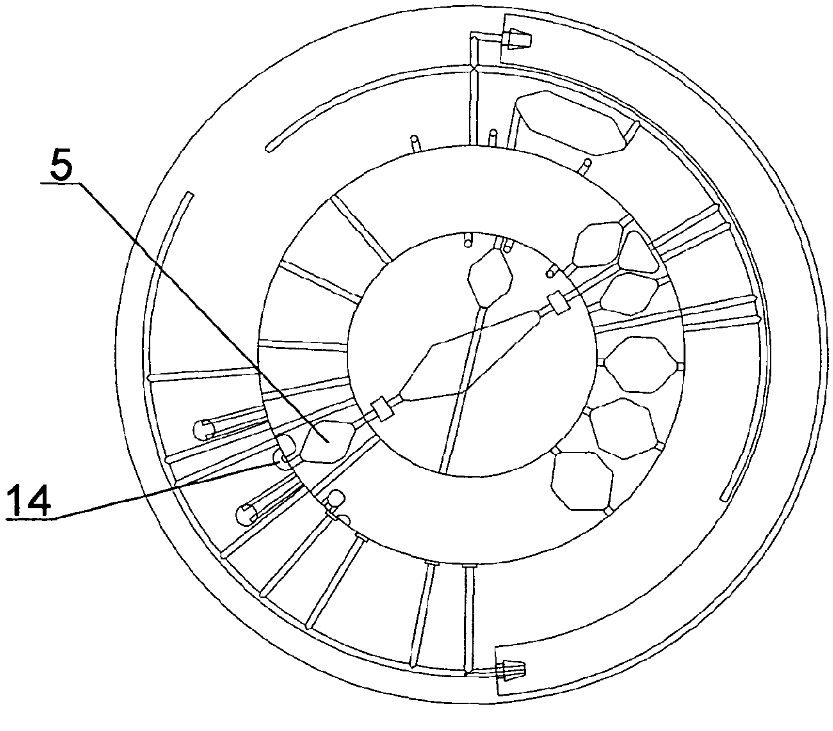
FIG. 12 shows a processing step while using the device according to FIG. 1.

The first and second support members 17, 18 are then rotated clockwise to connect the sixth depot chamber 5 with one of the measuring loops 14 (cf. FIG. 12). The elution buffer containing the DNA is then pumped into said measuring loop 14 until it is completely filled.

Figure 13:
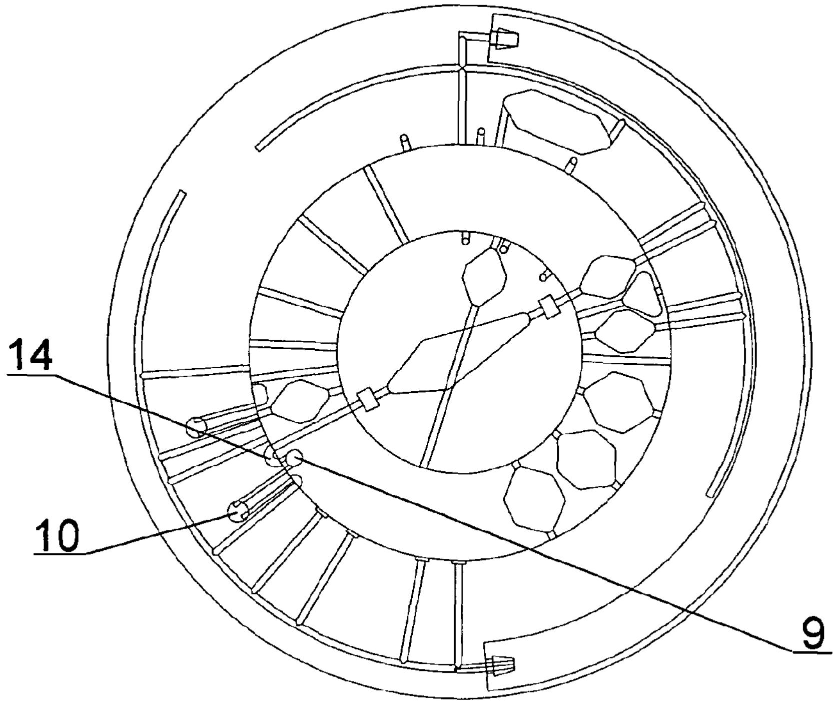
FIG. 13 shows a processing step while using the device according to FIG. 1.

A further rotational movement of the second support member 18 in a clockwise direction connects one of the mastermix depot chambers 9 with the now filled measuring loop 14 (cf. FIG. 13). The mastermix depot chamber 9 contains a mastermix of substances for the amplification and detection of nucleic acids. Each chamber 9 contains a mastermix for a specific amplification and detection of nucleic acids of interest e.g., from one or more bacterial species. Ten independent reactions (including internal control) can thus be run simultaneously using one cartridge. The mastermix from the mastermix depot chamber 9 along with the elution buffer containing the DNA is pumped via the measuring loop 14 into one of the PCR reaction chambers 10. In the presented embodiment, liquid reagents are used for the PCR although other formulations (encapsulated, freeze-dried, air-dried, etc.) are equally suitable and may be preferred due to their prolonged stability, even at elevated temperatures (e.g., during storage or transportation of the point-of-care device)—in this case, the volumes of the sixth depot chamber 5 and the measuring loops 14 may need to be adjusted in order to ensure a proper rehydration of the reagents.

The process as described in FIGS. 12 and 13 is repeated until all of the ten PCR reaction chambers 10 (of which only two are shown in the drawings) are filled with the substances.

Figure 14:
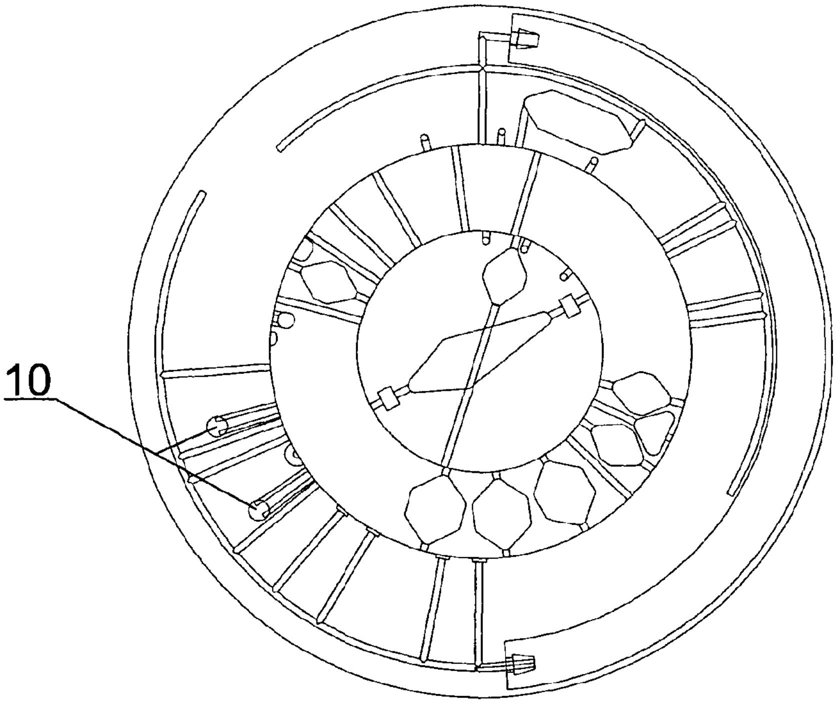
FIG. 14 shows a processing step while using the device according to FIG. 1.

As is shown in FIG. 14, the second support member 18 is then rotated clockwise until the conduits leading to the PCR reaction chambers 10 in the third support member 19 are disconnected from the conduits of the second support member 18.

For the sequence-based amplification of the nucleic acids, various methods may be applied, e.g., PCR, LCR (Ligase Chain Reaction), NASBA (Nucleic Acid Sequence-Based Amplification), TMA (Transcription-Mediated Amplification), HDA (Helicase-Dependent Amplification), etc.

In the presented embodiment, a PCR method is employed which allows a real-time quantitative identification of infectious agents in the patient's sample. A visual and/or an optical evaluation is possible as the third support member 19, which comprises the PCR reaction chambers 10, is at least partially made of a transparent polymer. An appropriate temperature profile for the PCR process is achieved by sliding different temperature zones, which are created in the base station, along the device. Some design features of the device facilitate rapid temperature adjustment within the PCR reaction chambers 10. These include the use of low thermal capacity polymer material for the device, high thermal conductivity of the PCR reaction chambers' walls that come into contact with the heating means as well as flat shape and high surface-to-volume ratio of the PCR reaction chambers 10. The heating means may also contain at least two additional temperature zones being set to temperatures, respectively, higher and lower than the temperatures provided in the given thermal cycling protocol. This allows for considerable shortening of the ramping times during the PCR and makes the system suitable for carrying out rapid quantitative PCR testing.

FIG. 15 shows a base station for use with the device according to FIGS. 1 to 14. The base station implements all functions the device itself does not provide, including:

- turning the first 17 and second support member 18;
- moving the roller element 23 for the elastic hose;
- positioning of the external permanent magnet 20;
- spinning of the external permanent magnet 20;
- positioning of temperature blocks 30 for heating the PCR process;
- controlled heating of the temperature blocks 30 for the PCR process steps (primer annealing, elongation and denaturation);
- controlled heating of sample chamber 6 (the heater integrated into cover plate 28) at 55° C. to 95° C.;
- providing a light source for fluorescence excitation; and
- fluorescence detection with a photodiode (optical unit 27).

For a circular movement of the first and the second support member 17, 18, a gear box 25 driven by an electric motor 26, is used. To connect the gear box 25 and the support members 17, 18, there are two times three carrier pins 31, 32 fixed on the gear box 25. Three respective holes (not shown) in the support members 17, 18 fit on the carrier pins 31, 32. The rotary movement of the gear box 25 is thereby transmitted to the support members 17, 18.

There is a mounting on a cogwheel for the roller element 23 of the hose pump, so that the roller element 23 will move circular about the central axis of the device along the elastic hose.

Figure 16:
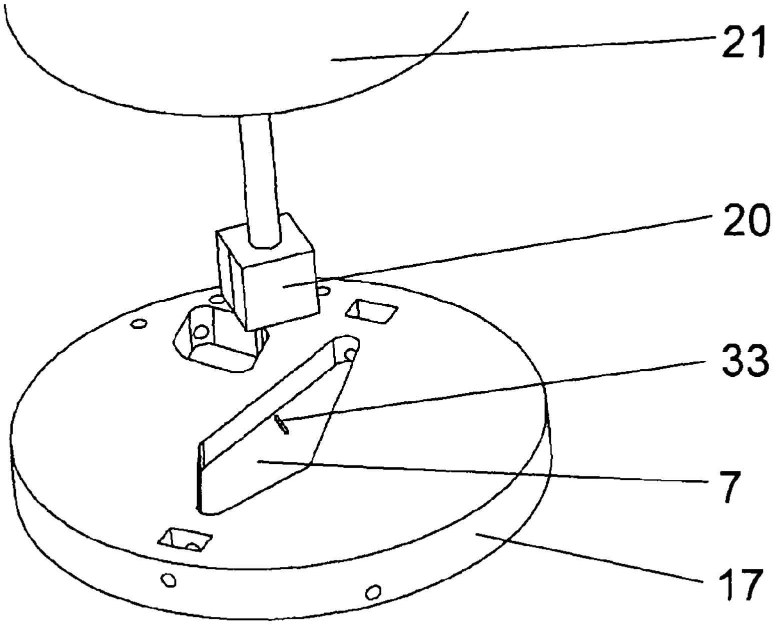
FIG. 16 shows the mixing device of the base station of FIG. 15.

In order to rotate the magnetic agitator 33 inside the process chamber 7, the base station comprises a mixing device (cf. FIG. 16). Said mixing device comprises an external permanent magnet 20, which is rotationally driven by a small electric motor 21. The external permanent magnet 20 is bonded to the axis of the electric motor 21. The north-south orientation of the external permanent magnet 20 is in a horizontal level, while the axis of the electric motor 21 is vertical. The magnetic agitator 33 inside the process chamber 7 of the first support member 17 thus follows the rotation of the external permanent magnet 20.

Figure 15A:
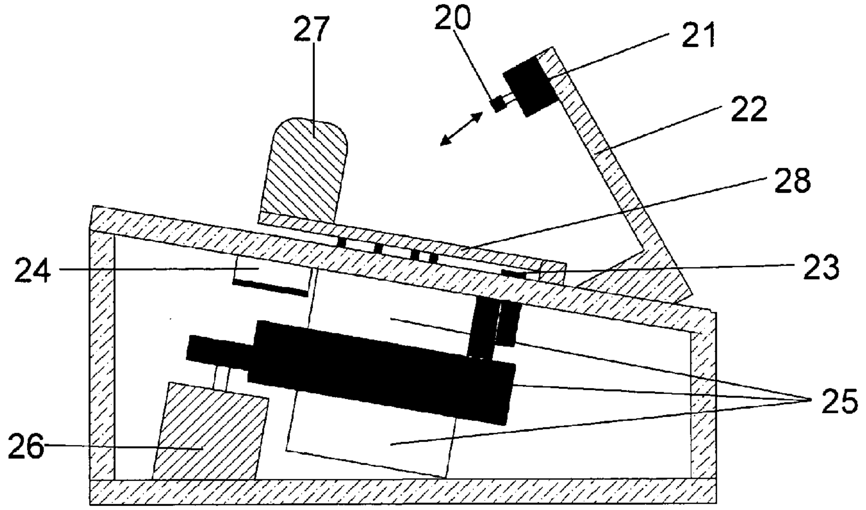
FIG. 15A shows a base station for use with the device according to FIGS. 1 to 14 in a side view.
Figure 15B:
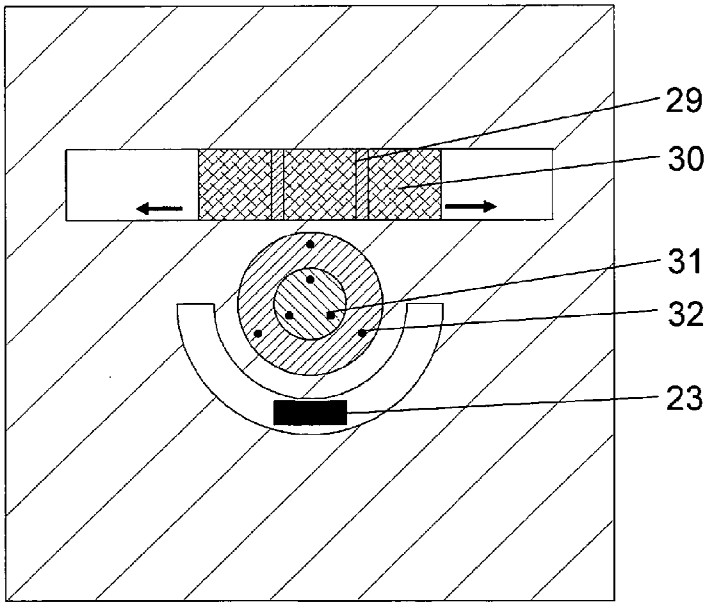
FIG. 15B shows the base station according to FIG. 15A in a top view.

To control the efficiency of stirring, the distance between external magnet 20 and process chamber 7 can be changed via a movable lifting arm 22 (cf. FIG. 15A). The motor 21 is mounted on the lifting arm. Distance and position of the external permanent magnet 20 can thus be controlled by moving the lifting arm.

At least two and actually three temperature blocks 30 alternate during the processing below the reaction chambers 10. Temperature blocks 30 are mounted sequentially therefor on a sliding plate 29. An electric motor 24 can move it in order to place an appropriate temperature block under the PCR reaction chambers 10. Temperature controllers assure that the temperatures are kept on constant levels. The temperature zones consist of blocks 30 heated with heating elements and temperature controlled with temperature sensors.

Alternative heating methods may be applied. For example, heating by means of hot fluids or "Peltier" elements is possible.

The device is mounted in the base station in an inclined alignment. Due to the gravitational force, this helps preventing the substance which enters e.g., the process chamber 7 to unintentionally exit the process chamber 7 and enter the hose pump.

Figure 17:
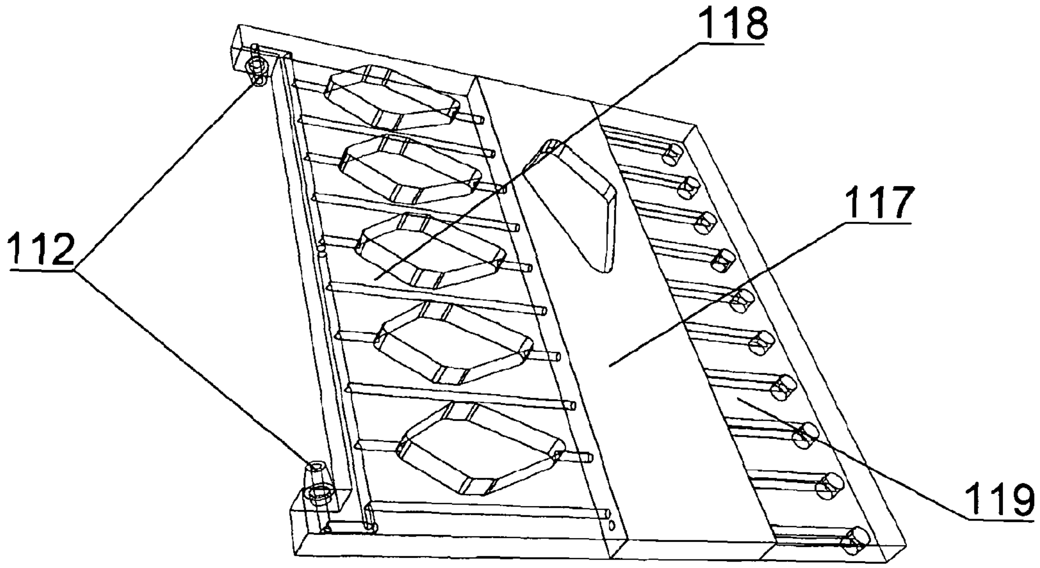
FIG. 17 shows an isometric view of the front side of a device according to the present invention in a second embodiment.

FIG. 17 shows a further embodiment of a device according to the present invention. This device comprises three support members which are movable with respect to each other. Unlike in the first embodiment shown in FIGS. 1 to 14, the three support members are linearly moveable with respect to each other. The arrangement of the chambers and further functional components is similar but not identical to the arrangement within the device according to the first embodiment. The first support member 117 comprises the sample chamber and the process chamber. The second support member 118 comprises different depot chambers, the elution chamber as well as two ports 112 for an elastic hose (not shown) as part of a pump element. Incorporated into the third support member 119 are the PCR reaction chambers and the measuring loops. The support members may be partially or completely made of a transparent material to allow a visibility of the chambers and conduits as is shown in FIG. 17 for the second support member 118.

Figure 18:
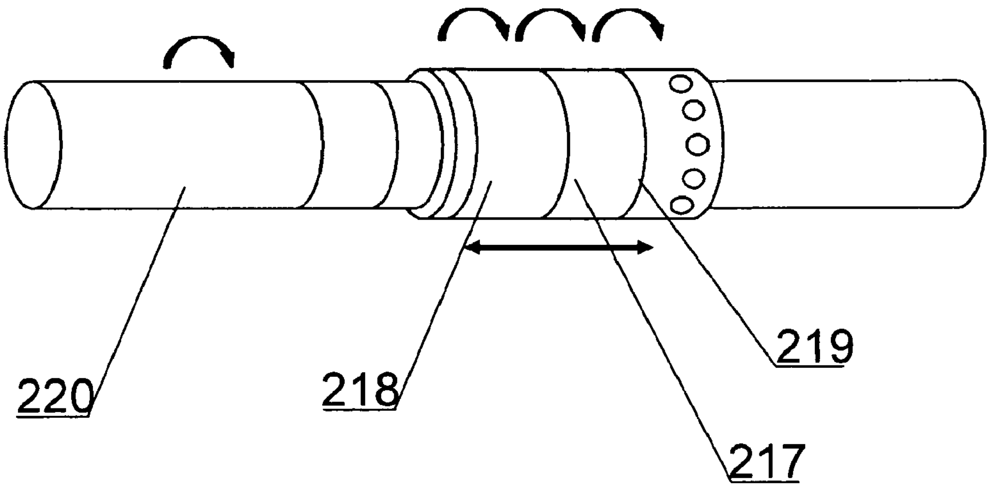
FIG. 18: shows an isometric view of a device according to the present invention in a third embodiment.
Figure 19:
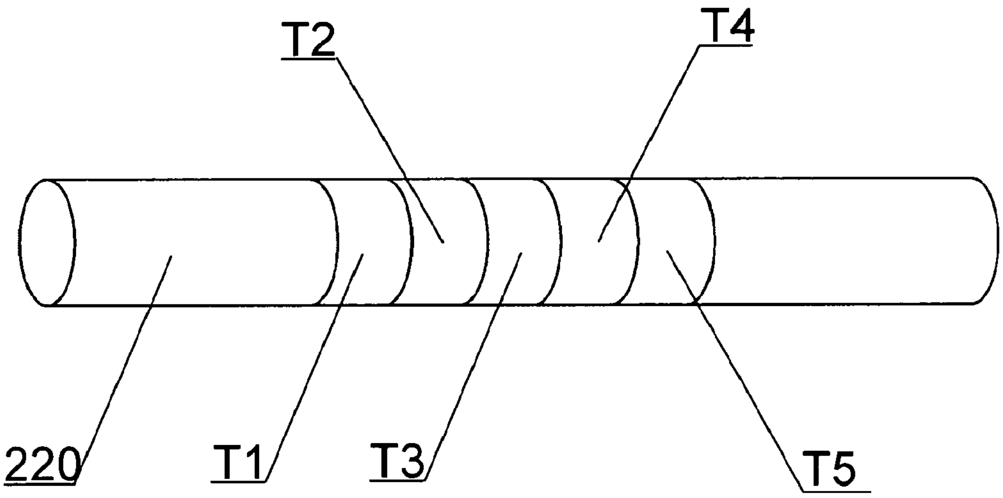
FIG. 19: shows an isolated element of the device according to FIG. 18.

A further embodiment of a device according to the present invention is shown in FIG. 18 and FIG. 19. The device comprises three annular support members 217, 218, 219, which are attached to a support bar 220 in a movable way (allowing a rotational movement as well as a movement in the longitudinal direction of the support bar). The three support members are further rotatable with respect to each other. Incorporated into the support bar 220 is a heating device (not shown) which creates different temperature zones $T_1$ to $T_5$. The arrangement of the different chambers and functional components in the first, second and third support member 217, 218, 219 corresponds to the arrangement within the device according to FIG. 17.

The present invention is not limited to embodiments described herein; reference should be had to the appended claims.

What is claimed is:

1. A microfluidic device of a microfluidic apparatus for analyzing a sample, the microfluidic apparatus comprising:

at last two support members comprising:

a first support member comprising, at east one first support member chamber confirmed to hold a fluid, the at least one first support member chamber comprising at least two first support member chamber openings comprising a first first support member chamber opening and a second first support member chamber opening, and at least two first support member conduits comprising a first first support member conduit, and a second first support member conduit, wherein, the first first support member conduit is connected to the first first support member chamber opening, and the second first support member chamber conduit is connected to the second first support member chamber opening;

a second support member comprising, at least one second support member chamber configured to hold a fluid, the at least one second support member chamber comprising at least two second support member chamber openings comprising a first second support member chamber opening and a second second support member chamber opening, and at least two second support member conduits comprising a first second support member conduit, and a second second support member conduit, wherein, the first second support member conduit is connected to the first second support member chamber opening, and the second second support member chamber conduit is connected to the second second support member chamber opening;

where the first support member and/or the second support member are configured to perform a movement with respect to each other so as to connect one of the at least two first support member conduits with one of the at least two second support member conduits and to thereby connect the at least one first support member chamber with the at least one second support member chamber;

a pump element arranged in at least one of the at least two support members, the pump element being configured, to connect to the at least one first support member chamber via one of the at least two first support member conduits and/or to the at least one second support member chamber via one of the at least two second support member chamber conduits, and to effect a transfer of the fluid from the at least one first support member chamber to the at least one second support member chamber and/or a transfer of the fluid from the at least one second support member chamber to the at least one first support member chamber, wherein, a connection comprising the at least one first support member chamber, the at least one second support member chamber, and die pump element via the at least two first support member conduits and the at least two second support member conduits creates a closed fluidic circuit.

2. The microfluidic device as recited in claim 1, wherein the at least one first support member chamber is a process chamber and the at least one second support member chamber is a depot chamber.

3. The microfluidic device as recited in claim 1, wherein the movement of the first support member and/or the second support member with respect to each other is at least one of a linear movement and a circular/rotational movement.

4. The microfluidic device as recited in claim 1, wherein, the at least two support members further comprises a third support member, and the second support member and/or the third support member are configured to perform a movement with respect to each other.

5. The microfluidic device as recited in claim 4, wherein, the third support member comprises the pump element and at least two third support member conduits comprising a first third support member conduit and a second third support member conduit, the at least two second support member conduits further comprise a third second support member conduit, the connection creating the closed fluidic circuit further comprises the at least two third support member conduits, the first support member, the second support member, and/or the third support member are configured to perform a movement with respect to each other so as to connect, the first first support member conduit with the first second support member conduit, the second second support member conduit with the first third support member conduit, the second third support member conduit with the third second support member conduit, and the third second support member conduit with the second first support member conduit, so as to thereby connect the at least one first support member chamber with the at least one second support member chamber and the pump element.

6. The microfluidic device as recited in claim 5, wherein, the first support member is arranged as a circular disc, the second support member is arranged as an annular disc and configured to surround the first support member, and the third support member is arranged as an annular disc and configured to surround the second support member.

7. The microfluidic device as recited in claim 6, wherein the base station further comprises a second drive configure to perform the movement of the second support member and/or the third support member with respect to the other.

8. The microfluidic device as recited in claim 1, wherein the pump element comprises an elastic hose.

9. A microfluidic apparatus for analyzing a sample, the microfluidic apparatus comprising:

a microfluidic device comprising at least two support members comprising:

a first support member comprising, at least one first support member chamber configured to hold a fluid, the at least one first support member chamber comprising at least two first support member chamber openings comprising a first first support member chamber opening and a second first support member chamber opening, and at least two first support member conduits comprising a first first support member conduit, and a second first support member conduit, wherein, the first first support member conduit is connected to the first first support member chamber opening, and the second first support member chamber conduit is connected to the second first support member chamber opening;

a second support member comprising, at least one second support member chamber configured to hold a fluid, the at least one second support member chamber comprising at least two second support member chamber openings comprising a first second support member chamber opening and a second second support member chamber opening, and at least two second support member conduits comprising a first second support member conduit, and a second second support member conduit, wherein, the first second support member conduit is connected to the first second support member chamber opening, and the second second support member chamber conduit is connected to the second second support member chamber opening;

wherein, the first support member and/or the second support member are configured to perform a movement with respect to each other so as to connect one of the at least two first support member conduits with one of the at least two second support member conduits and to thereby connect the at least one first support member chamber with the at least one second support member chamber; and a pump element arranged in at least one of the at least two support members, the pump element being configured, to connect to the at least one first support member chamber via one of the at least two first support member conduits and/or to the at least one second support member chamber via one of the at least two second support member chamber conduits, and to effect a transfer of the fluid from the at least one first support member chamber to the at least one second support member chamber and/or a transfer of the fluid from the at least one second support member chamber to the at least one first support member chamber, wherein, a connection comprising the at least one first support member chamber, the at least one second support member chamber, and the pump element via the at least two first support member conduits and the at least two second support member conduits creates a closed fluidic circuit; and and a base station comprising;

a first drive configured to perform the movement of the first support member or the second support member with respect to the other; and a pump drive.

10. The microfluidic apparatus as recited in claim 9, wherein, the at least two support members further comprises a third support member, the second support member and/or the third support member am configured to perform a movement with respect to each other, and the base station further comprises a second drive configured to perform the movement of the second support member and/or the third support member with respect to the other.

11. The microfluidic apparatus as recited in 10, wherein, the first support member is arranged as a circular disc the second support member is arranged as an annular disc and configured to surround the first support member, the third support member is arranged as an annular disc and configured to surround the second support member, and the base station further comprises a second drive configured to perform the movement of the second support member and or the third support member with respect to the other.

12. The microfluidic apparatus as recited in claim 9, wherein, the pump element comprises an elastic hose, and the base station comprises a roller element configured to perform a deformation movement along a length of the elastic hose so as to create a pumping pressure.

13. The microfluidic apparatus a recited in claim 9, wherein the base station further comprises:

a least one beating device configured to generate temperature zones in the base station for the microfluidic device; and a third drive configured to move the microfluidic device with respect to the at least one heating device.

14. A method of analyzing nucleic acids in the field of point-of-care applications with a microfluidic system, the microfluidic system comprising:

an analyzing device comprising at least two support members comprising:

a first support member comprising, at least one first support member chamber configured to hold a fluid, the at least one first support member chamber comprising at least two first support member chamber openings comprising a first first support member chamber opening and a second first support member chamber opening, and at least two first support member conduits comprising a first first support member conduit and a second first support member conduit, wherein, the first first support member conduit is connected to the first first support member chamber opening, and the second first support member chamber conduit is connected to the second first support member chamber opening;

a second support member comprising, at least one second support member chamber configured to hold a fluid, the at least one second support member chamber comprising at least two second support member chamber openings comprising a first second support member chamber opening and a second second support member chamber opening, and at least two second support member conduits comprising a first second support member conduit, and a second second support member conduit, wherein, the first second support member conduit is connected to the first second support member chamber opening, and the second second support member chamber conduit is connected to the second second support member chamber opening;

wherein, the first support member and/or the second support member are configured to perform a movement with respect to each other so as to connect one of the at least two first support member conduits with one of the at least two second support member conduits and to thereby connect the at least one first support member chamber with the at least one second support member chamber;

a pump element arranged in at least one of the at least two support members, the pump element being configured, to connect to the at least one first support member clamber via one of the at least two first support member conduits and/or to the at least one second support member chamber via one of the at least two second support member chamber conduits, and to effect a transfer of the fluid from the at least one first support member chamber to the at least one second support member chamber and/or a transfer of the fluid from the at least one second support member chamber to the at least one first support member chamber, wherein, a connection comprising the at least one first support member chamber, the at least one second support member chamber, and the pump element via the at least two first support member conduits and the at least two second support member conduits creates a closed fluidic circuit, the method comprising;

adding a nucleic acid sample into the analyzing device;

rotating the at least one first support member with respect to the at least one second support member, to connect one of the at least two first support member conduits with cue of the at least two second support member conduits, and to thereby connect the at least one first support member chamber with the at least one second support member chamber, and to connect the pump element to the at least oat first support member chamber via one of the at least two first support member conduits and/or to the at least one second support member chamber via one of the at least two second support member chamber conduits to form the closed circuit; and activating the pump element so as to cause a transfer of the nucleic acid sample from the at least one first support member chamber to the at least one second support member chamber or as to cause a transfer of the nucleic acid sample from the at least one second support member chamber to the at least one first support member chamber.

15. A method of analyzing nucleic acids in the field of point-of-care applications with a microfluidic system, the microfluidic system comprising:

an analyzing device comprising at least two support members comprising:

a first support member comprising, at least one first support member chamber configured to hold a fluid, the at least one first support member chamber comprising at least two first support member chamber openings comprising a first first support member chamber opening and a second first support member chamber opening, at least one of the at least one first support member chamber comprising a reaction chamber comprising a nucleic acid sample as the fluid, and at least two first support member conduits comprising a first first support member conduit, and a second first support member conduit, wherein, the first first support member conduit is connected to the first first sup ort member chamber opening, and the second first support member chamber conduit is connected to the second first support member chamber opening;

a second support member comprising, at least one second support member chamber configured to hold a fluid, the at least one second support member chamber comprising at least two second support member chamber openings comprising a first second support member chamber opening and a second second support member chamber opening, at least one of the at least one second support member chamber further comprising a depot chamber comprising a lysis solution as the fluid, and at least two second support member conduits comprising a first second support member conduit, and a second second support member conduit, wherein, the first second support member conduit is connected to the first second support member chamber opening, and the second second support member chamber conduit is connected to the second second support member chamber opening;

wherein, the first support member and/or the second support member are configured to perform a movement with respect to each other so as to connect one of the at least two first support member conduits with one of the at least two second support member conduits and to thereby connect the at least one first support member chamber with the at least one second support member chamber;

a pump element arranged in at least one of the at least two support members, the pump element being configured, to connect to the at least one first support member chamber via one of the at least two first sup ort member conduits and/or to the at least one second support member chamber comprising via one of the at least two second support member chamber conduits, and to effect a transfer of the fluid from the at least one first support member chamber to the at least one second support member chamber and/or a transfer of the fluid from the at least one second support member chamber to the at least one first support member chamber, wherein, a connection comprising the at least one first support member chamber, the at least one second support member chamber, and the pump element via the at least two first support member conduits and the at least two second support member conduits creates a closed fluidic circuit, the method comprising:

moving the reaction chamber with respect to the depot chamber and/or the pump element to connect the reaction chamber to the depot chamber and the pump element to form the closed circuit; and activating the pump element so as to cause a transfer of the nucleic acid sample from the reaction chamber to the depot chamber.

16. A method of analyzing nucleic acids m the field of point-of-care applications with a microfluidic system as recited in claim 14, wherein, the at least two support members further comprise a third support member, the third support member comprising, at least one third support member chamber configured to hold a fluid, the at least one thud support member chamber comprising at least two third support member chamber openings comprising a first third support member chamber opening and a second third support member chamber opening, and at least two third support member conduits comprising a first third support member conduit, and a second third support member conduit, wherein, the first third support member conduit is connected to the first third support member chamber opening, and the second third support member chamber conduit is connected to the second third support member chamber opening, wherein the first support member and/or the second support member and/or the third support member are configured to perform a movement with respect to each other so as to connect one of the at least two first support member conduits with one of the at least two second support member conduits and/or one of the at least two second support member conduits with one of the at least two third support member conduits and/or one of the at least two third support member conduits with one of the at least two first support member conduits and to thereby connect the at least one first support member chamber with the at least one second support member chamber and/or the at least one second support member chamber with the at least one third support member chamber and/or the at least one third support member chamber with the at least one first support member chamber, the third support member further comprising the pump element, the pump element being configured, to connect to the at least one first support member chamber via one of the at least two first support member conduits and/or to the at least one second support member chamber via one of the at least two second support member conduits and/or to the at least one third support member chamber via one of the at least two third support member conduits, and to effect a transfer of the fluid from the at least one first support member chamber to the at least one second support member chamber and/or from the at least one second support member chamber to the at least one third support member chamber and/or from the at least one third support member chamber to the at least one first support member chamber, wherein, a connection comprising the at least one first support member chamber, the at least one second support member chamber, the at least one third support member chamber and the pump element via the at least two first support member conduits, the at least two second support member conduits and the at least two third support member conduits creates a closed fluidic circuit, the method comprising;

adding a nucleic acid sample into the analyzing device;

rotating the at least one second support member with respect to the at least one first support member and third support member, to connect one of the at least two first support member conduits with one of the at least two second support member conduits and/or one of the at least two second support member conduits with one of the at least two third support member conduits and/or one of the at least two third support member conduits with one of the at least two first support member conduits, and to thereby connect the at least one first support member chamber with the at least one second support member chamber and/or the at least one second support member chamber with the at least one third support member chamber and/or the at least one third support member chamber with the at least one first support member chamber and the pump element, wherein, the connection comprising the at least one first support member chamber, the at least one second support member chamber, the at least one third support member chamber and the pump element via the at least two first support member conduits, the at least two second support member conduits and the at least two third support member conduits creates the closed fluidic circuit; and activating the pump element so as to cause a transfer of the nucleic acid sample from, the at least one first support member chamber to the at least one second support member chamber, and/or, the at least one second support member chamber to the at least one first support member chamber, and/or the at least one second support member chamber to the at least one third support member chamber, and/or the at least one third support member chamber to the at least one second support member chamber, and/or the at least one third support member chamber to the at least one first support member chamber, and/or the at least one first support member chamber to the at least one third support member chamber.

* * * * *